US 6,618,603 B2

(12) United States Patent
Varalli et al.

(10) Patent No.: US 6,618,603 B2
(45) Date of Patent: Sep. 9, 2003

(54) APPARATUS FOR MEASUREMENT AND CONTROL OF THE CONTENT OF GLUCOSE, LACTATE OR OTHER METABOLITES IN BIOLOGICAL FLUIDS

(75) Inventors: Maurizio Claudio Varalli, Milan (IT); Alessandro Poscia, Orvieto (IT)

(73) Assignee: Menarini Industrie Farmaceutiche Riunite S.r.L., Firenze (IL)

( * ) Notice: Subject to any disclaimer, the term of this patent is extended or adjusted under 35 U.S.C. 154(b) by 0 days.

(21) Appl. No.: 09/851,447

(22) Filed: May 7, 2001

(65) Prior Publication Data

US 2001/0041830 A1 Nov. 15, 2001

(30) Foreign Application Priority Data

May 8, 2000 (IT) ........................................ FI2000A0107

(51) Int. Cl.[7] .............................. A61B 5/05; G01N 27/26
(52) U.S. Cl. .................. 600/345; 600/347; 204/403.01; 435/14; 422/82.03
(58) Field of Search ................................ 600/345, 347, 600/365, 372; 128/920, 903–904; 204/403.01; 435/14; 422/82.03

(56) References Cited

U.S. PATENT DOCUMENTS

| 4,055,175 | A | * | 10/1977 | Clemens et al. ............... 604/66 |
| 4,206,755 | A | * | 6/1980 | Klein ........................ 604/28 |
| 4,526,569 | A | * | 7/1985 | Bernardi ..................... 604/4 |
| 5,174,291 | A | * | 12/1992 | Schoonen et al. ........... 128/632 |
| 5,711,861 | A | * | 1/1998 | Ward et al. ................. 204/403 |
| 5,791,344 | A | | 8/1998 | Schulman .................... 128/635 |
| 5,840,020 | A | * | 11/1998 | Heinonen et al. ............ 600/309 |
| 6,155,992 | A | * | 12/2000 | Henning et al. ............. 600/583 |
| 2002/0045808 | A1 | * | 4/2002 | Ford et al. ................. 600/347 |

FOREIGN PATENT DOCUMENTS

| DE | 4405149 | | 9/1994 | ............ A61B/5/14 |
| EP | 0134758 | | 3/1985 | ............ A61M/5/14 |
| EP | 5340741 A1 | | 3/1993 | ............ A61B/5/00 |
| EP | 940151 A1 | | 9/1999 | ............ A61M/1/34 |
| EP | 1048264 | * | 11/2000 | |
| IT | 4812983 | | 4/1983 | ............ A61B/5/00 |
| IT | 1231916 | | 5/1990 | ............ A61B/5/00 |

OTHER PUBLICATIONS

Spencer, "A Review of Programmed Insulin Delivery Systems", *IEEE Transactions on Biomedical Engineering,* vol. BME–28, No. 3, (Mar. 1981).

Pickup & Rothwell, "Technology and the Diabetic Patient", *Medical & Biological Engineering & Computing,* (Sep. 1984).

Alcock et al., "Technology for Continuous Invasive Monitoring of Glucose", 18th Annual International Conference by IEEE, Amsterdam, (1996).

* cited by examiner

*Primary Examiner*—John A. Jeffery
(74) *Attorney, Agent, or Firm*—Abelman Frayne & Schwab

(57) ABSTRACT

An apparatus for the continuous measurement of glucose and lactate in interstitial fluids including a glucose measurement cell, an A/D conversion block, a memory block and a bi-directional communication between the interface block and an external calculation unit.

27 Claims, 2 Drawing Sheets

APPARATUS FOR MEASUREMENT AND CONTROL OF THE CONTENT OF GLUCOSE, LACTATE OR OTHER METABOLITES IN BIOLOGICAL FLUIDS

FIELD OF THE INVENTION

This invention relates generally to the field of measurement transducers, and more specifically, to electronic circuits for glucose content measurement instruments for personal independent use.

Still more particularly, the invention relates to an apparatus for improved safety, flexibility of use, and improved measurement performance, in the near-continual determination of glucose or other molecules in extracellular fluids.

BACKGROUND OF THE INVENTION

STATE OF THE ART

The medical literature indicates the need to have dedicated instruments permitting almost continual measurement of the concentration in a patient's blood of certain specific molecules, such as glucose, lactate and others. Many such instruments dedicated to these measurements have been developed. One of the most serious drawbacks of prior devices has been the excessive invasiveness of known methods of measurement, which involve the need for direct access to a patient's blood vessels.

Research performed in this sector has, however, proven the validity of measurements of the concentration of such molecules in extracellular fluids, which measurements can be accurately correlated to the corresponding haematic concentrations.

The growing demand for control and cure of diabetes has led to an increase in the request by medical specialists for miniaturized measurement instruments that can be worn by patients and, which permit almost continual automatic and independent determination of the level of glucose in the blood or in intracellular fluids, for periods of from 24–48 hours to assess the circadian trend of this parameter during the normal behavioral activities of the patient.

Instruments of this type have been described in the literature and have been the subject-matter of patents, such as Italian patents IT1170375 and IT1231916. Such instruments, in fact, have been utilized to obtain measurements of glucose levels in artificial pancreases, as described for example in the article by W. J. Spencer—A review of Programmed Insulin Delivery Systems—published in the review IEEE Transactions on Biomedical Engineering, vol. BME-28, N.3, March 1981, page 237 ff., in which the measurement apparatus is represented schematically in blocks in FIG. 3 on page 239. There, the measurement section is described to be composed of three blocks, including a glucose measurement sensor, a minicomputer, and a measurement viewing system.

The article by J. C. Pickup and D. Rothwell published in the review Medical & Biological Engineering & Computing, 1984, 22, page 385 ff., paragraph 13 item "Glucose Sensors", describes two types of sensors to measure the glucose level, one for use implanted subcutaneously and one for extracorporeal use: Both of these solutions have certain advantages and drawbacks, which are briefly discussed below.

The implantable type, which comprises a sensor in direct contact with the extracellular fluids, is mounted on a miniaturized electronic circuit, performs the measurements inside the body of the patient, and transmits the results, in a suitably amplified and encoded form, to the extracorporeal memorization and processing system by means of an electromagnetic coupling, which enables the cutaneous barrier to be passed through without electrical contact, and which also permits the energy required for operation of the electronic circuit to be transferred from outside the body to inside the body.

The type of instrument in the implantable version has the advantage that the patient is totally separated from the external system, but such an instrument can only be applied if a measurement transducer, which is extremely stable over time is available. Although such a solution may be ideal for a therapeutic "artificial pancreas" for a single patient, it does not satisfy the clinical requirement of being capable of being fitted and removed after a short time, in order to be used in various patients for diagnostic purposes.

The second type of instrument, although particularly suitable for diagnostic controls, is limited to a few days operating capability, requires transcutaneous access by means of a needle to the bidirectional hydraulic circuit, which is formed using hollow fibres that permit an appropriate fluid solution to be pumped into a semipermeable fibre located in the body of the patient, where, through a filter membrane, the solution can collect the glucose molecules found in the extracellular fluid and convey the fluid sample containing the glucose to the measurement transducer fitted in the portable instrument.

Sampling is performed by means of a pump controlled by a microprocessor, operating according to a resident firmware type program, activated on the basis of choices and parameters selected by an external operator and which, after activation, operates totally automatically until subsequent action by the external operator. The microprocessor is capable of managing the hydraulic sample transfer system, and also of taking measurements, processing and storing them, managing any alarm threshold values, and transferring measurements on request to external computers for permanent storage and any further processing.

From a safety viewpoint, inasmuch as the portable instrument is equipped with a battery-operated power supply, there is no problem of user exposure to a main power supply, although this may become a consideration if using a cable to connect the portable instrument to the external computer, both during the phase in which the physician sets the parameters, and during the phase for transferring the measured values from the instrument on the patient to the external computer.

Safety standards for apparatus of this type, such as the current standards indicated in Japanese Law Decree Feb. 24, 1997 no. 46 and Feb. 26, 1998 no. 95, establish that this type of instrument is in Class IIa, in which there are extremely restrictive limits for leakage currents from the device and into the patient: These limits can be achieved by supplying power to the device through extremely low voltage batteries and using special electronic circuits, which permit limitation of the leakage current through the electrolytic conductor composed of the hydraulic tubes containing the solution pumped into the patient and by limiting the return solution to less than one hundredth of the allowed limit value. However, there remains the issue with regard to any leakage currents possibly carried by the connection cable from or to the external computer. The apparatus of the present invention further overcomes such last-mentioned problem through the use of a non-electrical connection.

With regard to the characteristics of the fluid sample taken for measurement, it is pointed out that this class of instruments is capable of handling complex organic fluid samples of any type, obtained from probes that are implanted transcutaneously, percutaneously, or implantable in the intravascular, subcutaneous or intraperitoneal areas, and also from extracorporeal fluid circuits, such as circuits for dialysis, for blood transfusions, for aphaeresis, and so forth. Moreover, the characteristics of the filters incorporated in the implantable hydraulic system define the dimensional limits of molecules able to be taken and permit the exclusion of any phenomena of interference and pollution of the sensor.

Glucose and lactate are considered to be the preferred analytes for the determination of which the apparatus of the present invention is particularly suitable.

SUMMARY OF THE INVENTION

It is a first object of the present invention to propose a new and more efficacious solution to the problem posed by the measurement of analytes found in interstitial fluids.

This object is attained with an apparatus according to the invention, characterised by the use of a pressure transducer for controlling the regularity of measurements and utilizing a transmission system for bidirectional transmission of information between an external computer and a measurement instrument of the second type, equipped with an enzymatic transducer outside the body of the patient.

According to the present invention, the transmission system is capable of guaranteeing total electrical isolation between the patient and external electrical circuits in any condition of use even in the circumstance of continual interfacing during the entire measurement phase.

A preferred embodiment of the apparatus of the present invention also includes the use of an alarm warning system capable of supplying a vibrational signal, which is more easily perceived by hearing-impaired patients, in addition to normal acoustic and luminous signals.

The apparatus of the present invention may be implemented by means of appropriate analog, digital or mixed circuits produced using techniques known in the prior art that use physical components and microprocessor programs, or by means of mixed systems of various types and complexities: These various embodiments are designated hereinafter as the hardware, software and firmware embodiments.

BRIEF DESCRIPTION OF THE DRAWINGS

The present invention will be described in detail with reference to the following drawings, wherein.

DETAILED DESCRIPTION OF EMBODIMENTS OF THE INVENTION

With reference to above-described block diagrams of the drawings, a description is now given of those embodiments of the apparatus of the present invention referred to above as instruments of the second type.

Figure 1:
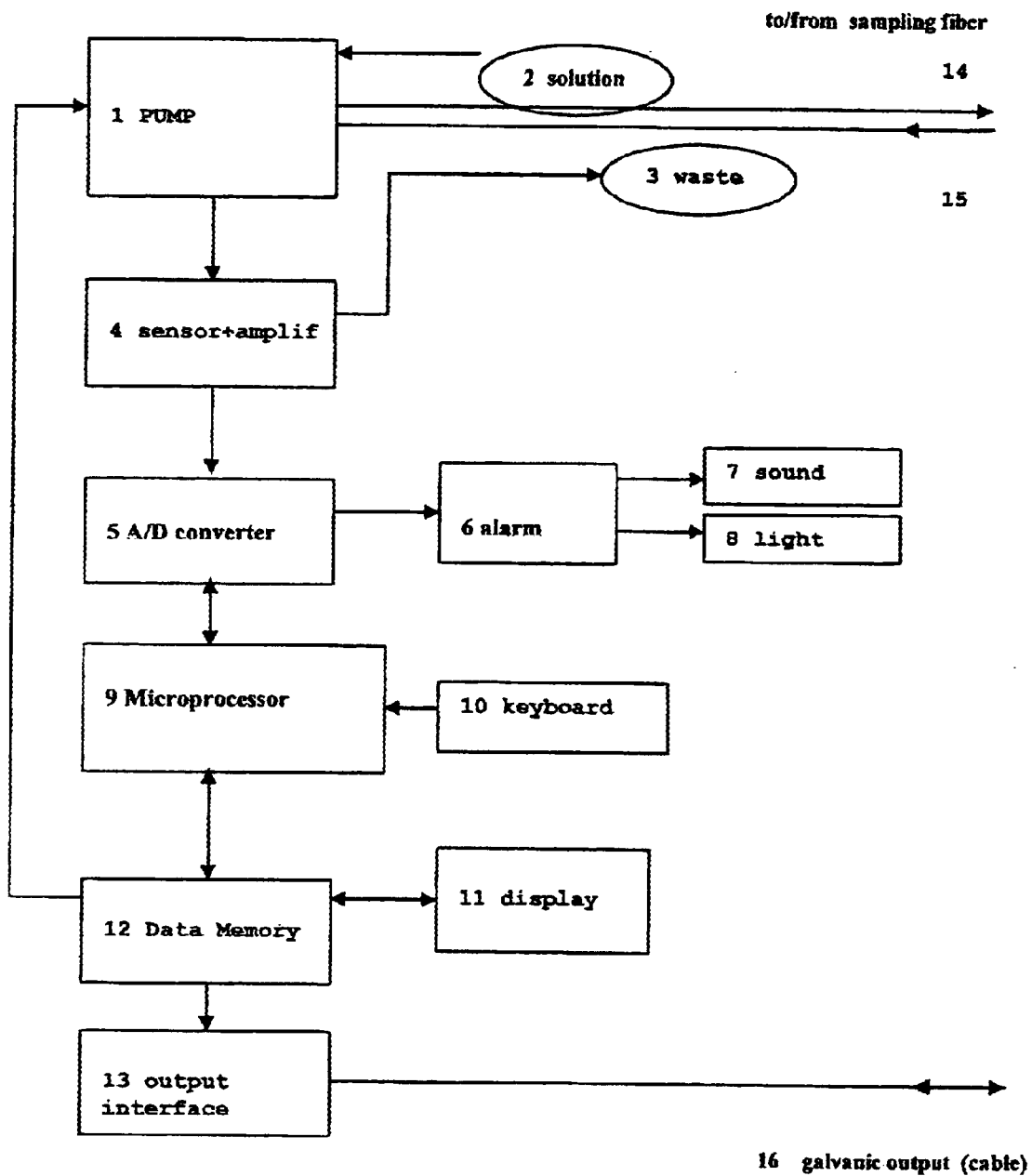
FIG. 1 is a block diagram of the functional units forming an instrument of the type previously known in the art for the near-continual measurement of glucose levels in organic fluids.

FIG. 1 is a block diagram of the functional units forming an instrument previously known in the art, as disclosed in the above-cited Italian patents.

The instrument is directed to the near-continual measurement of the glucose level in organic fluids and is equipped with a circulation pump for the solution from which the sample is to be taken by means of a subcutaneous hollow fibre probe.

With regard to FIG. 1, all the blocks forming the true measurement system are numbered from 1 to 13; the tubes for hydraulic transfer to and from the patient are indicated by numerals 14 and 15; and numeral 16 indicates the possible connection via cable between the instrument and an external data processing system.

Numeral 1 of FIG. 1 designates the hydraulic system comprising a driving pump, which is, for example, of the mechanical syringe, peristaltic, membrane, piezoelectric or any other type, and is used to transfer the solution taken from tank 2, which after being sent to a subcutaneous area of the patient through the capillary tube 14, where the sample of interstitial fluid containing a quantity of glucose proportional to the haematic quantity is taken by diffusion, transfers the sample to the measurement instrument through the capillary tube 15, and after measurement sends it to the discharge tank 3. The rate of flow, controlled by the specific microprocessor program, varies from zero to around 200 $\mu$L per minute, with a measurement time from 1 to 10 minutes, with measurements being taken once every 1 to 30 minutes. Measurement of the level of glucose in the sample is performed in block 4, comprising both the measurement section composed of immobilized enzyme that releases a quantity of oxygen proportional to the quantity of glucose found in the solution and an electrolytic cell for potentiometric measurements with platinum and silver electrodes that generate a current with an intensity proportional to the quantity of oxygen found, and an electronic amplification and current-voltage conversion circuit, the output signal of which, for example with an amplitude between 0 and 3 V, is proportional to the glucose level found in the sample being analyzed.

The enzymes utilized are GOD (glucose oxidase: from microorganisms and recombinant DNA), and LOD (lactate oxidase: from microorganisms and recombinant DNA). GOD from *Aspergillus Niger* is preferred.

This type of apparatus can be used in a similar way for other analytes by means of immobilization of suitable enzymes such as: HRP (peroxidase: from microorganisms and recombinant DNA), COD (cholesterol oxidase: from microorganisms and recombinant DNA). Immobilization with simple covalent bonds is typically selected.

The analog voltage signal is sent to block 5 equipped with an appropriate analog-digital conversion system with a resolution equal to or greater than 8 bit, from which the signal is sent in digital form to the microprocessor operating with 8 to 16 bit words with an internal RAM controlling the entire instrument 9, which can be controlled by the physician or patient using a keyboard 10 with operations and measurements viewed on the screen 11, said microprocessor also controlling both the motor of the pump that forces the flow into the capillary tubes 14 and 15, and into the measurement cell which is part of the measurement block 4, and the alarm management system 6 that operates the sound generator (for example a magnetodynamic or piezoelectric buzzer) and the luminous indicator 8, such as a LED or incandescent bulb or manages an alarm message on the digital screen, if provided.

The results of the measurements are stored in the data memory circuit 12, equipped with serial output control for connection to external units via the serial output interface block 13 equipped with appropriate circuits with opto-isolators (such as 4N25 components and similar) or with high isolation integrated circuits (such as the component MAX 252) installed to protect the patient. Connection to the external units is made by a cable 16.

Figure 2:
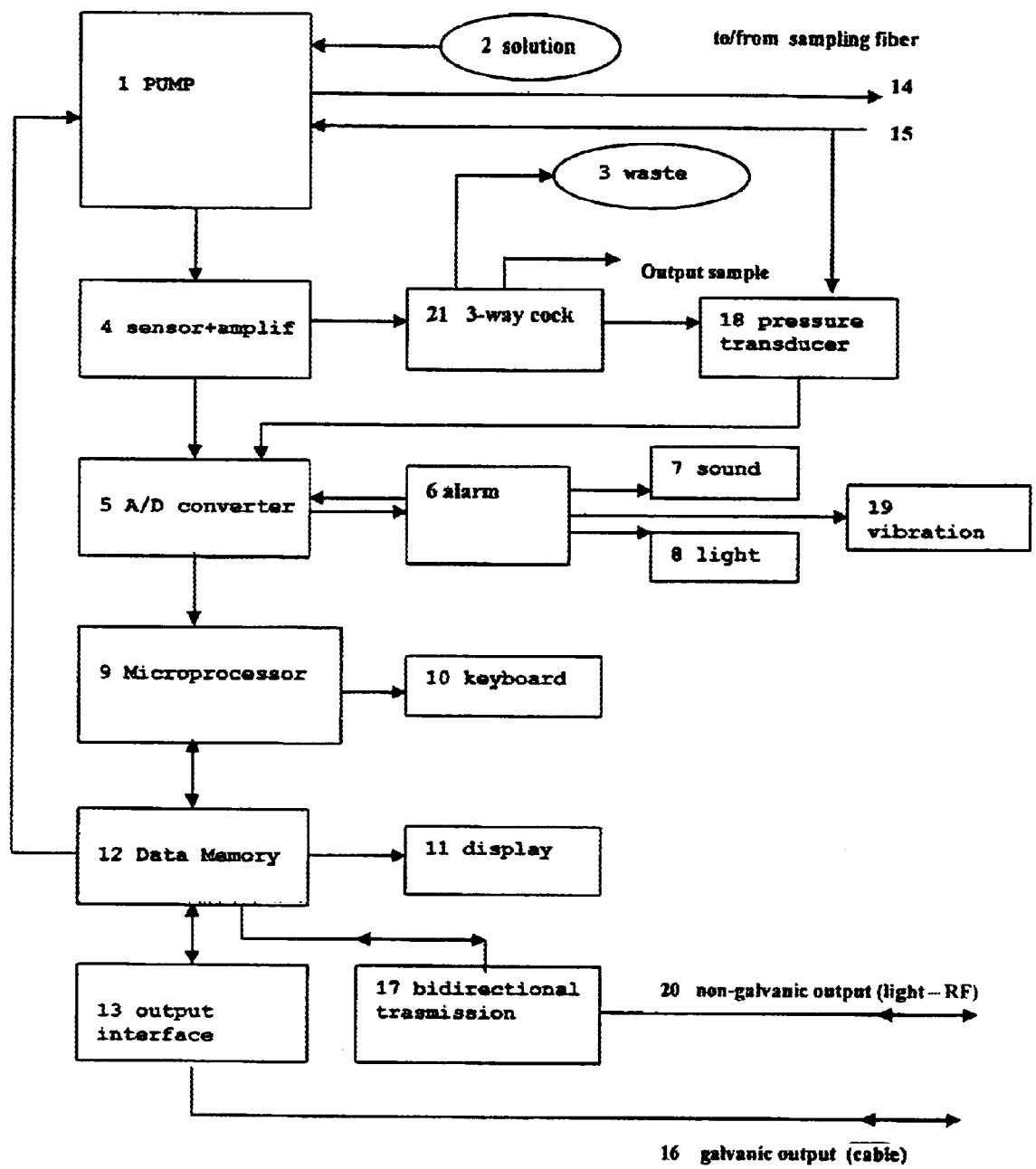
FIG. 2 is a block diagram of the functional units forming an instrument according to the present invention.

FIG. 2 represents the block diagram of the apparatus according to the invention.

The blocks identified from number 1 to number 13 are also found in FIG. 1, and the functions of each block correspond to those of the corresponding blocks already represented and previously described with reference to FIG. 1.

The block 17 comprises all the electronic components used to produce a bidirectional digital information transmission system via a beam of light, radio frequencies or other transmission systems described below and indicated by number 20, capable of permitting implementation of a bidirectional communication system from and to an external computer (not shown in the figure).

Advantageously, this connection is made without any electrical contact between the measurement instrument on the patient and the external computer, and can be put into practice via a photoelectric transducer, an IR optical transmission system, a Bluetooth radio frequency transmission system, a GSM system or via any other type of transmission protocol that the art may develop in the future, provided that this is capable of guaranteeing total electrical isolation of the external electrical circuits from the measurement system on the patient.

The optical transmission system, already known in information applications for connection between computers and peripheral units such as scanners and printers, based on a protocol named IrLAP, defined in detail by the Infrared Data Association and continually updated by this Association, described in detail in the publication IDA Ser. Infrared Physical Layer Link Specification, can for example use components such as the model HP HSDL-1001-011 optical transceiver formed of an integrated circuit in which information to be transmitted, which is received by and sent from the microprocessor as digital electrical signals by means of a serial connection, are utilised by an integrated circuit HP HSDL-7001 for electrical modulation and demodulation, in the HP HSDL-1001-011 optical transceiver, both of the infrared light source composed of the solid state light emitter and of the detector composed of a solid state photodiode.

The use of an infrared light optical system of this type as means of communication is an important factor in improving the safety for application contemplated in the connection system between the instrument on the patient and the external information system: this method of transmission, which is intrinsically characterised by electrical isolation impedance of an infinite value between patient and external information system, is superior to traditional systems, which unavoidably have a definite isolation impedance value between patient and external information system.

On the contrary, implementation by means of bidirectional transmission via radio, cannot be used without the possibility of serious problems as the system with electromagnetic waves is influenced by both active and passive electromagnetic interference.

The photoelectric system described for block 17 instead permits intrinsically safe bidirectional transmission capable of permitting transmission of information from the measurement unit to the external computer and transmission of commands and programs from said computer to the measurement unit, and also permits noteworthy simplifications and reductions in cost to be attained in the phases to qualify the instrument and in those to check and measure the quality during industrial production.

These same advantageous results can also be obtained with transmission systems based on the protocol for BLUE-TOOTH® radio frequency transmission, for GSM® radio frequency systems, or on other protocols that development in the art may offer and which already are available or will be available in addition to the traditional serial transmission system on a RS232 cable.

In the apparatus according to the invention, the interface block of output 13 can be produced so that it has the same number of output modules as the aforesaid different types of interface that can be used, such as BLUETOOTH and GSM radio frequency transmission systems, etc.

According to a preferred form of embodiment of this apparatus, the interface output block 13 comprises a single interface circuit and a plurality of modules that can be individually inserted on said circuit. This solution, compared to the one in which there are the same number of output modules as the various types of interface, in addition to being more flexible, also permits a reduction in overall dimensions and expenditure.

Another advantageous characteristic of the apparatus embodies a block 18 comprising a pressure measurement transducer with all the relevant electronic components for implementation of a continual pressure measurement system in the hydraulic system for circulation of the transfer fluid of the sample to be measured and, as a non-limiting example, this transducer can be produced with the component, model no. ADP 3131, manufactured by Mitsubishi.

The information available for each measurement is thus composed both of the voltage value proportional to the content of glucose of the sample and of the value of the pressure in the circuit at the time of measurement, bearing in mind that this value may be positive or negative in relation to the external pressure and is transferred to the microprocessor by means of the analog-digital converter of block 5.

Availability of the pressure value is extremely important as this permits discarding of measurements with values that can be influenced by the presence of transitory irregularities in the hydraulic circuit, such as gaseous microbubbles, which make the reading unstable, a break in the seal of the hydraulic circuit caused by damage to tubes or microfibres, which make the pressure value drop towards zero.

Availability of the pressure value thus permits medical staff to rapidly identify irregularities of various types, such as the presence of micro-bubbles, damage to the hydraulic system or hollow fibre, the development of clots or obstructions of biological or mechanical origin, deposits developing in the microtubes, and so forth.

Another advantageous characteristic of the apparatus embodies a block 19 comprising the electromechanical and electronic components used to create a vibrational alarm system, which in addition to the acoustic and luminous systems already found in blocks 10 and 11, can significantly improve detection of an alarm signal by the patient and, as a non-limiting example, this type of alarm system can be produced by utilizing a micromotor with eccentric mass, such as model A6B-09/W3B3, manufactured by CIK.

According to a particular form of embodiment of this invention, the two tanks, represented in the diagram by blocks 2 and 3 and respectively containing the perfusion fluid and the discharge fluid, may be replaced by a single bag or tank divided into two compartments by an impermeable and deformable dividing wall, so that said compartments perform the functions of tanks 2 and 3 described above. This form of embodiment of the invention with a single tank has the advantage of reducing the overall dimensions compared to the apparatus with two separate bags or tanks.

As the quantity of discharge fluid entering the tank 3 is greater than the quantity flowing out of tank 2 due to the amount of extracellular fluid taken for measurements, in the solution with a single tank it is preferable for the volume of the compartment performing the functions of tank 3 to be greater than the volume of the tank performing the functions of tank 2.

The single tank may also be provided with an appropriate asymmetrical two-way hydraulic connector to guarantee correct connection of the feed and discharge tubes.

The measurement cell included in block 4 is preferably produced as an element that can be inserted and replaced provided with two electrical pressure contacts through which the current flows, the value of which is determined by the glucose content in the measurement fluid. As the value of said current with the cell polarized with a voltage of around 0.65 Volts is equivalent to a few nanoAmperes, the equivalent internal resistance is of tens of megaohms: the measurement circuit of this apparatus must thus have an isolation resistance value of on order at least twice the order of the internal resistance value of the cell.

For this purpose the apparatus of the invention may be provided with a coupling system with pressure contacts with extremely high isolation against which the measurement cell is blocked elastically, which carry the electrical signal to the electronic amplifier.

Alternatively, the block 4 may include an element to be inserted composed of an assembly of the measurement cell and relevant electronic amplifier of the transconductance type, which permits conversion of current signals with an amplitude equivalent to picoAmperes into voltage signals with an amplitude of fractions of a Volt, such as the circuit described in figure 24 of the Application Note AN-63 of the National Semiconductor Corporation. The electronic circuit of the amplifier can also have a calibration circuit for standardizing the output signal dV/dG when used with transducers characterized by different sensitivity values of the current output in relation to the concentration of glucose dI/dG.

The solution described above is specifically advantageous as it permits the use of interchangeable transducers, that can be calibrated against variations in sensitivity in the period of life by means of a simple measurement with calibrated glucose solutions, and also permits the construction of the apparatus to be simplified, excluding parts with high isolation resistance. In the apparatus of the invention the output tube 15 is preferably equipped with a three-way cock 21, that can be manoeuvered by means of a suitable safety system, which in the "closed" position permits transit of the flow of discharged fluid from the measurement cell towards the discharge tank 3, while in the open position permits said flow to be diverted towards the outside to be collected in a container for any control analysis. Advantageously, this analysis can be used to assess the dilution coefficient of the extracellular fluid by measuring the concentration of molecules with a limited molecular weight capable of freely crossing the various filters in the measurement system, such as the molecules of electrolytes like sodium or potassium, or even molecules of hormones with low molecular weight: in this way it is possible to check at any time the percentage of dilution of the measured sample, which must be established with extreme precision to determine the quantities of molecules, such as glucose, found in the undiluted extracellular fluid.

This solution permits a decrease in the number of haematic measurements required to determine the coefficient of proportionality.

What is claimed is:

1. An apparatus for the near-continual measurement of the quantity of analytes found in an interstitial biological fluid, comprising a hydraulic circulation system (1) capable of taking a solution from a tank (2) and sending the solution through a capillary tube (14) into a subcutaneous area of a patient, from where an appropriately filtered sample of interstitial fluid is taken through a capillary tube (15) and sent to a block (4) provided with a measurement cell for measuring the glucose level and, after measurement, the sample is sent to a discharge (3);

in which an analog voltage signal corresponding to the measurement performed is sent from the block (4) to an analog-digital conversion block (5) from where the signal is again sent in digital for to a data memory (12) of a microprocessor control unit provided with an alarm management system (6) and an output interface block (13), which includes a block (17) for bidirectional transmission between the interface block (13) and an external calculation unit of the digital signal, such that there is not electrical contact between the interface block (13) and the external calculation unit.

2. The apparatus according to claim 1, wherein the bidirectional transmission block (17) transmits the digital signal to the external calculation unit by means of a beam of light.

3. The apparatus according to claim 2, wherein the transmission block (17) is equipped with transceiver optical circuits.

4. The apparatus according to claim 3, wherein the transceiver optical circuits are optical transceivers formed of an integrated circuit in which information to be transmitted is received by and sent from the microprocessor as digital electrical signals by means of a serial connection.

5. The apparatus according to claim 3, wherein the transmission block (17) is equipped with appropriate modulation circuits of the transceiver optical circuits so that luminous signals transmitted and received comply with at least one infrared optical communication protocol.

6. The apparatus according to claim 1, in which the bi-directional transmission block (17) transmits the digital signal to the external calculation unit by means of radio frequencies according to CCITT rec. X 25 protocol.

7. The apparatus according to claim 1, further comprising a system (18) for continuous measurement of the pressure in the hydraulic circulation system (1) for the transfer fluid of the sample to be measured.

8. The apparatus according to claim 1, wherein the alarm management system is equipped with a vibrational alarm device (19).

9. The apparatus according to claim 1, wherein the hydraulic system (1) includes a driving pump selected from the group consisting of:
a mechanical pump;
a syringe;
a peristaltic pump;
a membrane pump;
and a piezoelectric pump.

10. The apparatus according to claim 1, wherein after the solution is sent to a subcutaneous area of the patient through a capillary tube (14) said sample of interstitial fluid is taken by diffusion through a filter membrane.

11. The apparatus according to claim 1, wherein the sample is sent to the discharge tank (3) at a flow rate ranging from 5 to 200 µL per minute.

12. The apparatus according to claim 1, wherein the tank (2) and the discharge (3) are formed of two compartments of a single tank, which is divided in two by an impermeable and deformable dividing wall, such that the compartments perform the functions of the tank (2) and of the discharge (3).

13. The apparatus according to claim 12, wherein a volume of the compartment of the single tank performing the function of the discharge (3) is greater than the volume of the compartment of the single tank performing the function of the tank (2).

14. The apparatus according to claim 1, wherein the analyte is selected from the group consisting of glucose and lactate.

15. The apparatus according to claim 14, wherein measurement of the level of analyte in the sample is taken by means of an immobilized enzyme which releases a quantity of oxygen proportional to the quantity of analyte in the solution.

16. The apparatus according to claim 15, wherein the enzyme is selected from the group consisting of:

glucose oxidase (GOD), produced from microorganisms or recombinant DNA;

and lactate oxidase (LOD), produced from microorganisms or recombinant DNA;

and further wherein the enzyme is immobilized with simple covalent bonds.

17. The apparatus according to claim 16, wherein the analyte is glucose and the enzyme is GOD, produced from the microorganism *Aspergillus Niger*.

18. The apparatus according to claim 1, wherein the measurement cell of block (4) is a cell for performing potentiometric measurements, utilizing platinum and silver electrodes, which generate a current of an intensity proportional to the quantity of oxygen present; and further wherein the electronic circuit for amplification and current—voltage conversion has an output voltage signal with an amplitude of from 0 to 3 V, with the amplitude of the output voltage signal being proportional to the level of analyte in the sample being analysed.

19. The apparatus according to claim 1, wherein the measurement cell of block (4) includes a coupling system with pressure contacts against which the measurement cell is blocked elastically, so that a value of an isolation resistance of the measurement circuit is at least twice as great as a value of an internal resistance of the cell.

20. The apparatus according to claim 1, wherein the measurement block (4) includes a transconductance electronic amplifier, having interchangeable transducers and a calibration circuit.

21. The apparatus according to claim 1, wherein block (5) has a resolution of at least 8 bits.

22. The apparatus according to claim 1, wherein interface block (13) is provided with a patient-protective electrical feature to prevent electrical shock or injury to the patient, the feature being selected from the group consisting of: use of a serial output together with appropriate circuits with single opto-isolators; and use of isolating integrated circuits.

23. The apparatus according to claim 22, wherein the patient-protective electrical feature is a serial output with appropriate circuits with single opto-isolators.

24. The apparatus according to claim 22, wherein the patient-protective electrical feature employs solating integrated circuits.

25. The apparatus according to claim 1, wherein interface block (13) is provided with a single interface circuit.

26. The apparatus according to claim 1, wherein interface block (13) is provided with a plurality of interface modules.

27. The apparatus according to claim 1, wherein capillary tube (15) is equipped with a three-way cock with an open position and a closed position, which when in the closed position permits transit of the flow of discharge fluid from the measurement cell to the discharge tank (3), and when in the open position permits the flow to be externally diverted.

* * * * *